United States Patent
Pepper

(10) Patent No.: US 7,259,859 B2
(45) Date of Patent: Aug. 21, 2007

(54) TERAHERTZ MODULATION SPECTROMETER

(75) Inventor: David M. Pepper, Malibu, CA (US)

(73) Assignee: HRL Laboratories, LLC, Malibu, CA (US)

(*) Notice: Subject to any disclaimer, the term of this patent is extended or adjusted under 35 U.S.C. 154(b) by 320 days.

(21) Appl. No.: 10/764,036

(22) Filed: Jan. 23, 2004

(65) Prior Publication Data

US 2005/0162658 A1   Jul. 28, 2005

(51) Int. Cl.
*G01B 9/02* (2006.01)
*G01J 3/45* (2006.01)

(52) U.S. Cl. .................................. 356/451; 356/484

(58) Field of Classification Search ............... 356/484, 356/451
See application file for complete search history.

(56) References Cited

U.S. PATENT DOCUMENTS

| | | | |
|---|---|---|---|
| 4,297,035 A * | 10/1981 | Bjorklund | 356/402 |
| 4,733,397 A | 3/1988 | Gallagher et al. | 372/26 |
| 4,765,736 A | 8/1988 | Gallagher et al. | 356/300 |
| 6,873,405 B2 * | 3/2005 | Kido et al. | 356/121 |
| 2002/0036814 A1 * | 3/2002 | Mueller et al. | 359/180 |

OTHER PUBLICATIONS

"50 Years Development of the Microwave Mixer for Heterodyne Reception", Oxley, IEEE Transactions on Microwave Theory and Techniques, Mar. 2002, pp. 867-876.*

Ali, M.E., et al., "Optical Mixing with Difference Frequencies to 552 GHz in Ultrafast High Electron Mobility Transistors," *IEEE Photonics Technology Letters*, vol. 12, No. 7, Jul. 2000, pp. 879-881.

* cited by examiner

Primary Examiner—Gregory J. Toatley, Jr.
Assistant Examiner—Patrick Connolly
(74) Attorney, Agent, or Firm—Ladas & Parry

(57) ABSTRACT

A method and apparatus for detecting spectral properties of a sample are disclosed. Electromagnetic radiation in the Terahertz range emitted from a first laser source is modulated and combined with electromagnetic radiation emitted from a second laser source. The frequency spectrum of the combined signal comprises sidebands which can be tuned to resonate with the frequency spectrum of the sample. Tuning of the sidebands is obtained by tuning the first laser source, the second laser source, or the modulation frequency.

26 Claims, 5 Drawing Sheets

TERAHERTZ MODULATION SPECTROMETER

BACKGROUND

1. Field

The present invention relates to modulation spectroscopy. More specifically, it relates to a tunable system to be used as a narrowband modulation spectrometer operating at Terahertz frequencies.

2. Related Prior Art

Systems are known, which make use of FM modulation spectroscopy (FMS). These FMS systems involve devices in the visible or near-IR spectral regions. Typically, a single laser source is FM modulated, either directly or via an external modulator, to produce the desired sidebands, centered about the optical carrier. However, in order to realize more versatile FMS systems or communications or RADAR systems, it is necessary to modulate an optical or RF source over a wide excursion at a high frequency. The required frequency excursion and modulation frequency (e.g., modulation index or number of sidebands) are dictated by the spectroscopic feature to be detected in the case of FMS or by the system bandwidth in the case of a communications link. Although such systems exist in the optical and infrared regimes as well as in the RF domain (GHz range), they have not been realized in the THz regime.

Modulation of a THz carrier cannot be realized via direct modulation of a THz source, since such high-frequency modulators, i.e. having a frequency modulation $\Delta$ in the THz range, are not available, especially in the case of high-modulation index applications, where an external modulator would require many waves of phase shift at high frequencies, or, an oscillator would require a large fractional bandwidth, in the case of direct frequency modulation of a THz oscillator.

U.S. Pat. No. 4,733,397 to Gallagher discloses a resonant cavity optical modulator, and U.S. Pat. No. 4,765,736 to Gallagher discloses a frequency modulation spectroscopy technique using dual frequency modulation and detection. However, in both documents the modulation is imposed onto a single laser beam. Therefore, should FMS in the THz regime be performed by means of the techniques disclosed in Gallagher, it could only be performed by a single THz source, whose carrier frequency is that of the THz oscillator itself. Further, the Gallagher documents do not disclose how to generate all the required modulation sidebands required for the FMS applications, like, for example, remote sensing.

In order to operate at Terahertz frequencies, two kinds of approaches have been followed.

According to a first approach, a pulsed, broadband Terahertz probe is employed, to detect amplitude and/or phase shifts of a sample in a given volume. The broadband Terahertz radiation is generated using short-pulsed lasers, incident either onto a photoconductive switch or onto a nonlinear optical difference-frequency mixer. The detection portion employs either a matching photoconductive switch or an electro-optic crystal. The system is broadband, with about 10% to 50% bandwidth, because of the use of pulsed lasers, which contain many frequency components. As a consequence, the system has limitations in terms of sensitivity, selectivity and resolution.

According to a second approach, narrowband measurements of the amplitude and/or phase shift experienced by a probe beam in the presence of the given species are effected. A fixed-frequency narrowband source is employed (e.g. a free-running narrowband oscillator, or direct modulation of a laser using a high-frequency stable modulator) or alternatively a tunable narrowband source. An example of a narrowband tunable source involves a pair of laser sources, whose frequency difference corresponds to the desired Terahertz frequency, and is incident upon a fast detector (e.g. group III-V FETs or HEMTs—high electron mobility transistors), with the output coupled in a microwave antenna. This system is narrowband and can be tuned by tuning the lasers. However, the pair of lasers are tuned to a fixed frequency difference. This can generate a THz output signal, which contains only a single non-tunable frequency component corresponding to the frequency difference of the two lasers. As a consequence, it is not useful for high-resolution spectroscopy, since, in many cases, the desired spectral feature to be sensed is obscured by other spurious absorption features (like broadband absorption and scattering), which are not able to be compensated by a system using a single carrier frequency.

As a consequence, there is a need for a system that generates a multi-frequency THz output beam to enable ultra-high-precision spectroscopy and trace-compound detection.

SUMMARY

The present invention overcomes the prior art problems, enabling to realize extremely narrowband THz radiation.

According to a first aspect of the present invention, two laser beams are mixed in a detector, in order to generate a narrowband Terahertz source. A tunable FM modulator is also used, in order to generate the required tunable sidebands. Preferably, narrowband lasers, i.e. lasers operating in continuous or long-pulse format, are provided.

According to a second aspect of the present invention, an apparatus is disclosed comprising: a first laser, emitting a first beam having a first frequency; a second laser, emitting a second beam having a second frequency, the difference between the first frequency and the second frequency being in a Terahertz range; a mixer, located downstream of the first laser and the second laser, the mixer producing a mixed signal; and a modulator modulating at least one beam between the first beam and the second beam.

According to a third aspect of the present invention, an apparatus is disclosed comprising: a first laser, emitting a first beam having a first frequency; a second laser, emitting a second beam having a second frequency, the difference between the first frequency and the second frequency being in a Terahertz range; a frequency modulator, having a modulation frequency, for frequency modulating one beam between the first beam and the second beam; and a mixer, having as an input the frequency modulated one beam and the other beam and outputting a mixed signal.

According to a fourth aspect, an apparatus is disclosed comprising: a first laser, emitting a first beam having a first frequency; a second laser, emitting a second frequency modulated beam having a carrier frequency and a modulation frequency, the difference between the first frequency and the carrier frequency being in a Terahertz range; and a mixer, having as an input the first beam and the second frequency modulated beam and outputting a mixed signal.

According to a fifth aspect, an apparatus is disclosed comprising: a first laser, emitting a first beam having a first frequency; a second laser, emitting a second beam having a second frequency, the difference between the first frequency and the second frequency being in a Terahertz range; a modulator, for modulating in amplitude one beam between the first beam and the second beam; and a mixer, having as an input the amplitude modulated one beam and the other beam and outputting a mixed signal.

According to a sixth aspect, an apparatus is disclosed comprising: a first laser, emitting a first beam having a first frequency; a second laser, emitting a second amplitude modulated beam having a carrier frequency, the difference between the first frequency and the carrier frequency being in a Terahertz domain; and a mixer, having as an input the first beam and the second amplitude modulated beam and outputting a mixed signal.

According to a seventh aspect, an apparatus is disclosed comprising: a first laser, emitting a first beam having a first frequency; a second laser, emitting a second beam having a second frequency, the difference between the first frequency and the second frequency being in a Terahertz range; a high electron mobility transistor (HEMT) having a first terminal, a second terminal, and a photoconductive region on which the first beam and the second beam impinge; and a modulator having a modulation frequency, for modulating an intermediate signal having an intermediate frequency inferior to the first frequency and the second frequency to obtain a modulated signal, the modulated signal input to the first terminal of the HEMT, wherein the second terminal of the HEMT outputs a mixed signal having a frequency spectrum depending on the first frequency, the second frequency, the intermediate frequency, and the modulation frequency.

According to an eighth aspect, a method is disclosed comprising: providing a first laser beam having a first frequency; providing a second laser beam having a second frequency, the difference between the first frequency and the second frequency being a Terahertz frequency; modulating at least one beam between the first beam and the second beam; and mixing the first beam and the second beam to generate a mixed signal.

The fields in which the present invention can be applied relate to high-precision spectroscopy and local or remote sensing of trace-compound species, like, for example, explosive detection, bio-chemical rogue agent sensing, bio-medical diagnostics, nondestructive testing (NDT) of materials, THz imaging, as well as narrowband communication and radar systems at high carrier (THz) frequencies.

A first advantage of the present invention is that high-resolution and high-sensitivity narrowband detection of trace-compound species is obtained. Moreover, detectivity and resolution are enhanced when compared with existing approaches.

A further advantage of the present invention relates to the rapid tuning of the THz carrier frequency by simply tuning the frequency difference of the pair of optical sources so that the remote sensor can be quickly scanned across many spectral features of interest.

An additional advantage relates to the ability for rapid tuning of the sideband frequencies and control of the modulation index for adaptive fine-tuning of the THz spectrometer.

All these features employ photonics devices and control, as opposed to THz-based devices, such as THz oscillators and THz modulators, which are not wideband and are not robust.

The present invention goes far beyond the prior art single-frequency approach, by employing two lasers and modulating one or both of the lasers, either by direct modulation of the lasers themselves, or via an external modulator for one or both of the lasers.

In either case, the laser beam(s) obtained through the present invention consist of several frequency components, which, when combined in a high-speed detector, result in a THz carrier with many well-defined subcarriers.

This multi-frequency THz output beam, which can possess AM, FM or other characteristic sidebands, can enable ultra-high-precision spectroscopy and trace-compound detection when probing a given or unknown species or pollutant.

In another application, the information on the sidebands can also be used to relay information to a remote site, much like that of a communications link. Thus, the modulation imposed onto one or both of the lasers can consist of useful data to be relayed to another station. The basic frequency offset $\omega_1-\omega_2$ between the lasers can be chosen to correspond to an atmospheric window, so that long propagation paths can be realized for the communications link. The modulation on the lasers can also be formatted (like spread spectrum encoding or chirped modulation) to realize THz-based radar interrogation systems and similar apparatuses.

As a consequence, the fact that semiconductor lasers (as well as fiber lasers) can be frequency-modulated over large frequency ranges enables the present invention to encode very high modulation index information, namely single as well as multiple subcarriers with large frequency deviations.

According to the preferred embodiment of the present invention, FM modulation spectroscopic technique is applied to the Terahertz regime. Parts per billion (10-9) detectability have been demonstrated using FM modulation spectroscopy in the optical domain, whereby a single source, typically in the visible or infrared spectral sources, is FM modulated.

The present invention employs a pair of optical sources, and, moreover, imposes the high-modulation-index information on the optical leg of the system, which is then down-converted to the THz range via the fast detector. Since the down-conversion process conserves the magnitude of the frequency offsets between the subcarriers, the required fractionally large subcarriers are thus realized at THz frequencies using existing state-of-the-art lasers and photonic modulation techniques.

The frequency of the THz carrier can be easily tuned over a wide range.

The desired sideband structure (frequency separation and number of sidebands, or modulation index) can be generated and rapidly controlled by imposing modulation onto one or both of the lasers, via direct modulation of the lasers themselves or via external optical modulators.

DETAILED DESCRIPTION

FIGS. 1 and 2A-2C show schematical diagrams of a prior art arrangement operating at Terahertz frequencies.

Figure 1:
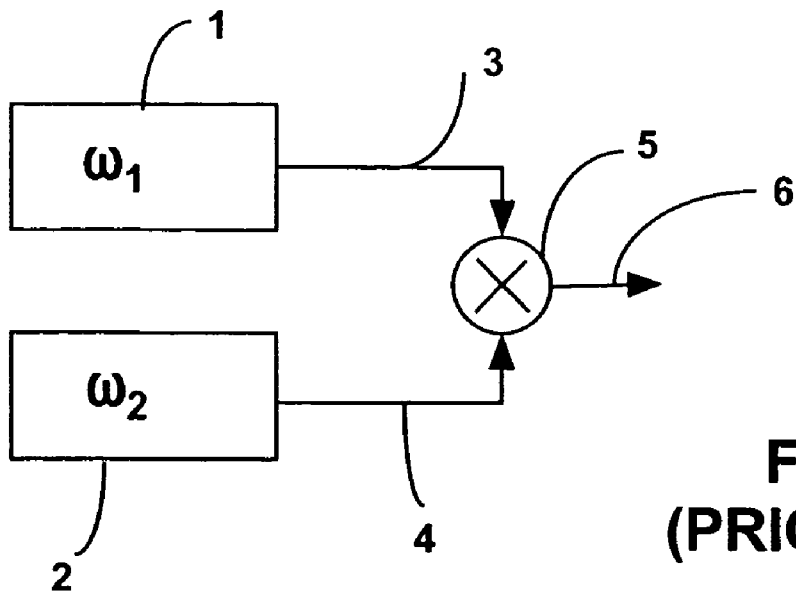
FIG. 1 is a schematic diagram showing a prior art device operating in the Terahertz frequency range.
Figure 2A:
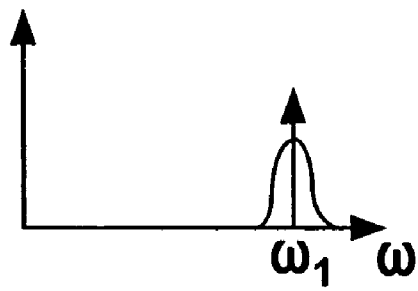
FIGS. 2A-2C show frequency domain graphs relating to the system of FIG. 1.
Figure 2B:
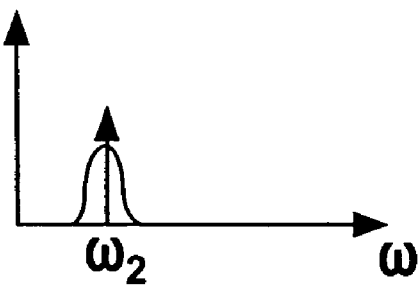
Figure 2C:
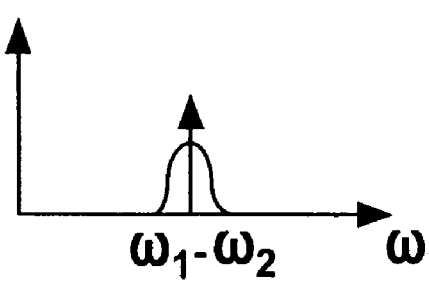

In FIG. 1, a first narrowband laser 1 outputs a beam or signal at a first frequency $\omega_1$, while a second narrowband laser 2 outputs a beam or signal at a second frequency $\omega_2$. The frequency-domain graph of FIG. 2A shows the graph of the signal at position 3 of FIG. 1. The frequency-domain graph of FIG. 2B shows the graph of the signal at position 4 of FIG. 1. As shown in FIGS. 2A and 2B, the lasers 1 and 2 are narrowband, meaning with that the width of the frequency band of the laser is typically in a range of about 1 KHz to about 10 MHz. For example, laser diodes, fiber lasers, or diode-pumped solid state lasers can be used.

The two lasers 1 and 2 are offset in frequency by the frequency $\delta\omega=\omega_1-\omega_2$. Both beams impinge on a mixer 5. Given the square-law property of a photodetector (not shown) placed downstream of the mixer 5, there will be signal components at the difference frequency of the lasers. Assuming that the bandwidth of the photodetector is sufficiently high, the output of the photodetector will consist of a single narrowband Terahertz output signal, limited in linewidth to that of the lasers, as shown in graph of FIG. 2C, which shows the frequency-domain graph of the signal at position 6 of FIG. 1. The mixer 5 of FIG. 1 is typically a narrowband mixer, and provides an output signal at $\delta\omega$, with a bandwidth equal to that of the lasers, which is typically of the order of many MHz.

Lasers 1 and 2 can, for example, have a wavelength from about 1 μm to about 1.5 μm. Assuming that $\lambda_1=1$ μm and $\lambda_2=1.5$ μm, it follows that $f_1=300$ THz, $f_2=200$ THz and $f_1-f_2=100$ THz, a value in the Terahertz regime.

The system operates with standard Terahertz antennas, beam directors and focusing elements, not shown.

As already discussed in the introductory portion of the present application, the system of FIG. 1 has limitations in terms of sensitivity, selectivity and resolution.

Figure 3:
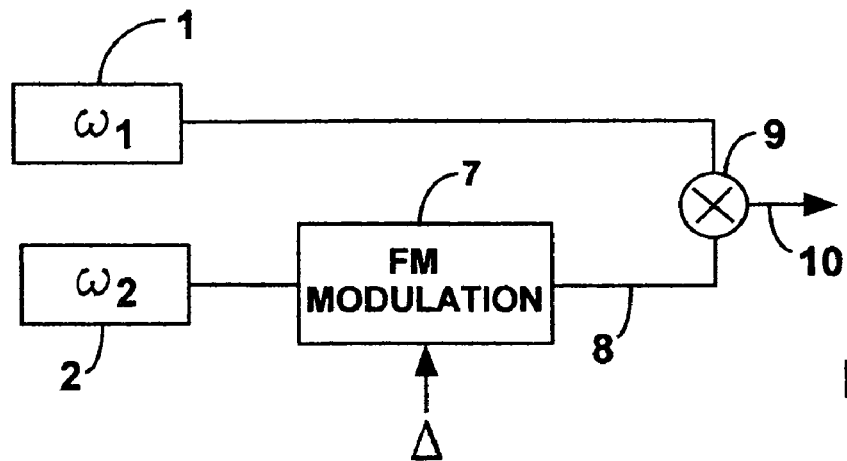
FIG. 3 shows a schematic diagram of the system according to the present invention.

FIG. 3 shows a preferred embodiment of the present invention, in which one of the two lasers, for example laser 2, is frequency modulated through a modulator 7, having a modulation frequency $\Delta$, before being mixed with laser 1 in a mixer 9. According to the numerical example provided before, the modulator 7 will handle a 200 THz carrier frequency. Optical modulators of this kind are common in the photonics industry and will not be described here in detail.

Figure 4A:
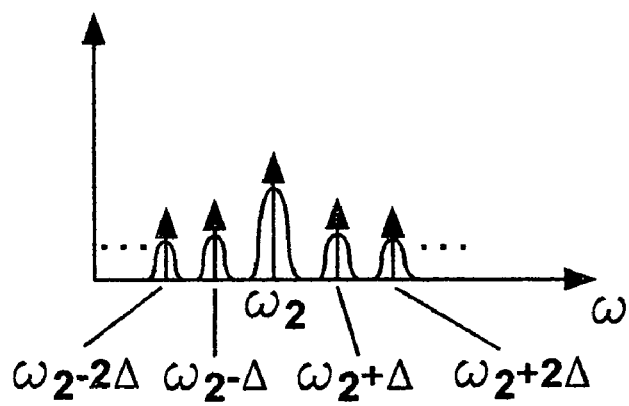
FIGS. 4A and 4B show frequency-domain graphs relating to the system of FIG. 3.

The graph of FIG. 4A shows the output 8 of modulator 7. The value of $\Delta$ can usually range from 1 MHz to 1 GHz.

Figure 4B:
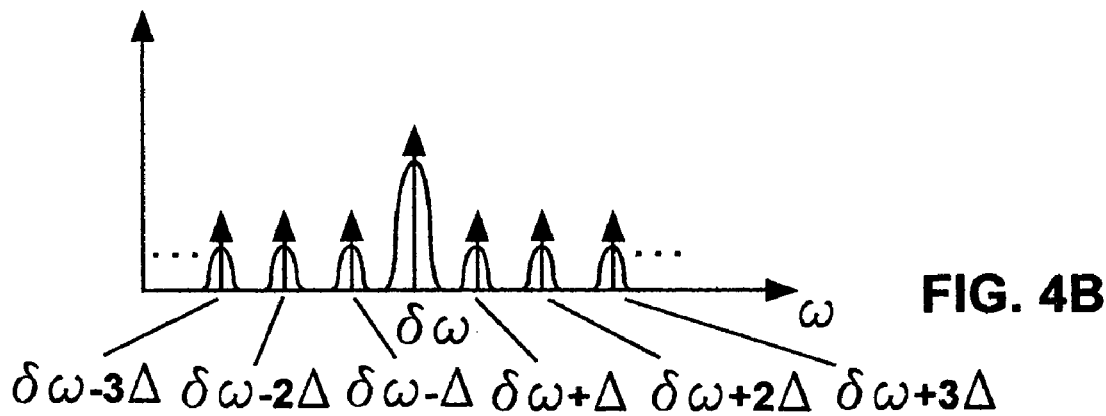

The graph of FIG. 4B shows the output 10 of mixer 9, containing at least three frequency components: the Terahertz carrier ($\delta\omega$) and symmetric sidebands, displaced in frequency by the modulation frequency $\Delta$ ($\delta\omega-\Delta$ for the first sideband and $\delta\omega+\Delta$ for the second sideband) and centered at the Terahertz carrier. By increasing the FM modulation depth, sidebands which are additional to the first and second sideband can be generated. The depth, or modulation index M, can range from 1 to 1,000. FIG. 4B shows the additional sidebands $\delta\omega\pm2\Delta$, $\delta\omega\pm3\Delta$. The variation of the modulation index depends on the desired number of sidebands required for a given application (e.g., the spectroscopic details of the species to be sensed, including its linewidth, spectral broadening, and energy level structure), as well as on the dispersive properties of the propagation path. When the modulated first laser is combined with the second laser, the resultant THz frequency components are therefore the following: $\delta\omega$, $\delta\omega\pm\Delta$, $\delta\omega\pm2\Delta$, $\delta\omega\pm3\Delta$, ... $\delta\omega\pm M\Delta$, where the carrier frequency $\delta\omega$ represents the frequency difference of the two lasers: $\delta\omega=\omega_1-\omega_2$.

The mixer 9 of FIG. 3 has a bandwidth accommodating the frequency range of the THz carrier $\delta\omega$ and the sidebands, i.e. a range from $\delta\omega-M\Delta$ to $\delta\omega+M\Delta$.

Alternative embodiments can be provided, where the first laser is frequency modulated, or where both lasers are frequency modulated.

The lasers can be modulated either directly, by modulating the current in a laser diode or modulating the laser cavity length, or externally, via a variety of off-the-shelf electro-optic or acousto-optic modulators.

Figure 5:
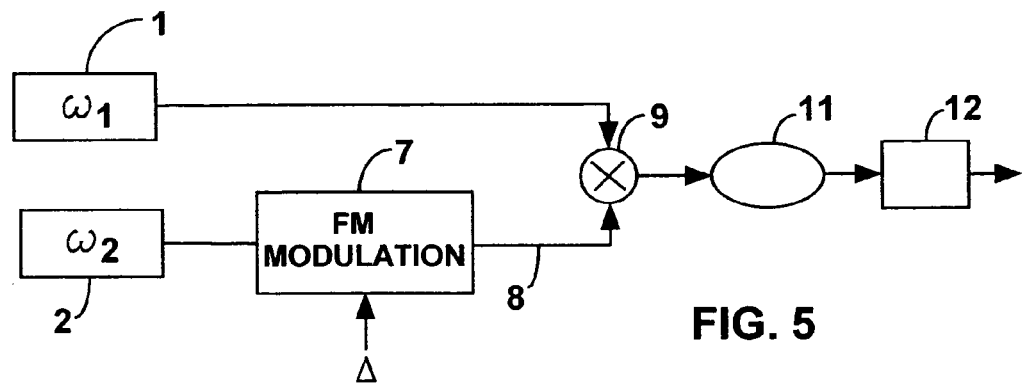
FIG. 5 shows a schematic diagram of the system according to the present invention when applied to a sample whose spectral properties have to be measured.

FIG. 5 shows a preferred mode of employment of the present invention, where a sample 11, whose spectral properties have to be measured, is placed between the mixer 9 and a square-law detector 12, such as a photodiode.

The sample size is dependent on the application and the sample material. For example, in the case of spectral analysis of gaseous samples, the size of the sample container can vary from several mm in path length to many meters for laboratory/medical analysis, to kilometers or more where samples in outdoor ranges are analyzed. Solid samples can also be analyzed, which can range in size from microns (particulates) to many cubic centimeters, and can include industrial samples for manufacturing, which may contain hidden defects, as well as specially treated assays for chemical, biological and medical analysis that may be treated with state-specific adsorbants for compound identification. Liquids can also be used as samples, and be also prepared with species-specific enzymes for various medical diagnostic applications. The size of the liquids can range from droplets to liters.

The system is arranged so that one of the FM sidebands of FIG. 4B will be resonant with the spectral feature of interest. This means that, by tuning the FM excursion, the sidebands can be tuned across the special feature of interest, so that photocurrent showing the presence of such feature will be output by a detector 12.

In other words, when the modulated Terahertz beam probes a species of interest, the resonant sideband will experience an amplitude and phase shift relative to the off-resonant carrier and to the other sideband. The modulated Terahertz output is then detected with the photodetector 12 of FIG. 5. Given the properties of the FM sidebands (they are 180° out of phase with respect to each other), differential phase and amplitude signals among the sidebands can be detected.

The measurement according to the present invention is a null measurement. This means that in absence of a differential signal the output will be zero, because the sidebands are equal and opposite in phase. Therefore, the system can be very sensitive relative to a single-frequency narrowband or broadband Terahertz measurement. Moreover, since all the three (or more) frequency components traverse the same probe volume, a common-mode rejection system is realized.

Figure 6A:
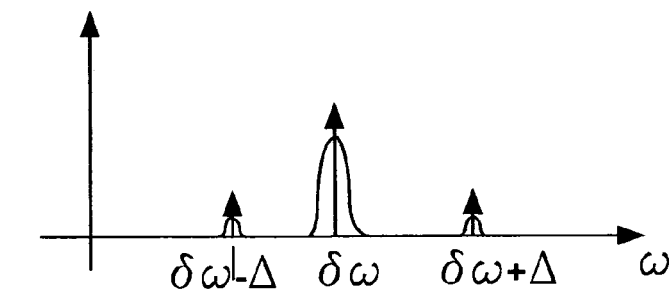
FIGS. 6A-6C show frequency-domain graphs relating to the tunability of the system according to the present invention.
Figure 6B:
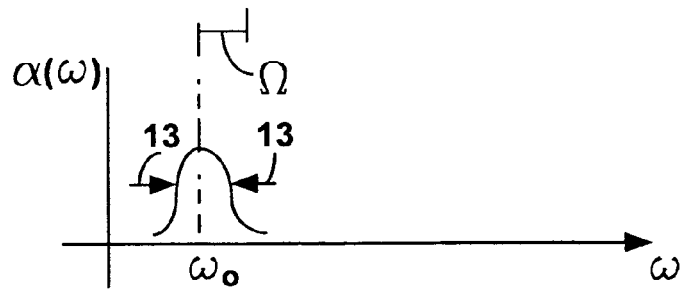
Figure 6C:
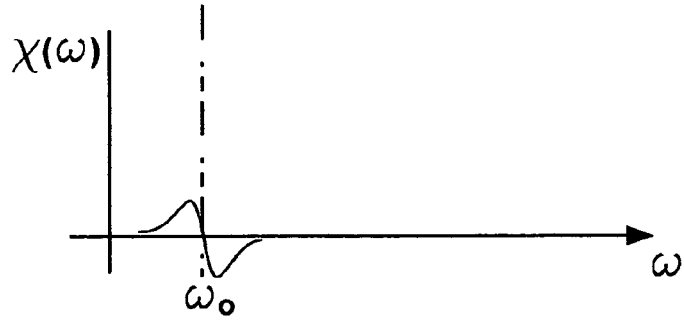

FIGS. 6A-6C show these features in greater detail. The graph of FIG. 6A shows the central frequency and the first sidebands of the output of the mixer 9, similarly to what is shown in FIG. 4B. FIG. 6B shows a possible absorption spectrum $\alpha(\omega)$ of the sample or species 11 to be detected. The center frequency of the absorption spectrum of the graph of FIG. 6B is indicated with $\omega_0$. The width 13 indicates the spectral linewidth $\Delta\omega_0$ of the absorption spectrum $\alpha(\omega)$. FIG. 6C shows the dispersion spectrum $\chi(\omega)$ of the species 11 to be detected, namely the first derivative of the graph of FIG. 6B.

The spectral linewidth $\delta\omega_0$ corresponds to the range of frequencies that the sample 11 absorbs. For example, the center frequency $\omega_0$ may be 50 THz, and the full width, half-maximum absorption indicated by the lines 13 of FIG. 6B may span a range from 49 THz to 51 THz. Thus, in this case, $\delta\omega_0$ has a value of 2 THz. Therefore, the $\delta\omega-\Delta$ THz source is tuned over the range of the absorption feature (in this case, 2 THz), so that the feature can be spectrally "mapped" out, or identified. Tuning of the $\delta\omega-\Delta(=\omega_1-\omega_2-\Delta)$ source can be done by tuning the optical modulator frequency $\Delta$ or by tuning the optical frequencies $\omega_1$, $\omega_2$ of one or both of the lasers. Preferably, before detailed tuning is performed, the absolute frequency of the THz tunable source is adjusted so that it nearly overlaps the absorption feature to start with. In other words, the frequency offset $\Omega$ should preferably be small before fine tuning is started. Additionally, it is also preferable that the linewidth $\delta\omega_1$, or $\delta\omega_2$ of the lasers is much less than $\delta\omega_0$. Otherwise, the THz "probe" frequency will be too "smeared" out to perform a high resolution measurement of the feature to be probed.

The frequency tuning range is dependent on the specific lasers employed, and can usually range from 1% to greater than 50% of the nominal THz carrier frequency, which is the difference in the frequency of the pair of lasers.

By comparing the graphs of FIGS. 6A and 6B, a small frequency offset $\Omega$ can be noticed between the value $\delta\omega-\Delta$ of the first sideband of the graph of FIG. 6A and the center frequency $\omega_0$ of the absorption spectrum of the graph of FIG. 6B. In order to overcome this offset and allow resonation to occur, the frequency difference $\delta\omega$ or the laser FM modulation frequency excursion $\Delta$ can be tuned over a range of the order of $\delta\omega_0$.

Typically, the Terahertz frequencies are in the 1 to 1000 THz range and the FM sidebands are in the 100 MHz to 5 GHz range. Moreover, the linewidth $\delta\omega_1$ of the first laser or the linewidth $\delta\omega_2$ of the second laser can be less than 1 MHz (and as small as 1 KHz) and can be tuned over a large range, in the order of nm or more.

This results in a high-precision and tunable spectrometer. These parameters are all feasible with commercial-off-the-shelf components.

Wideband FMS techniques can also be applied, by employing FM modulators with greater modulation index or via direct FM-modulation of the laser itself.

Figure 7:
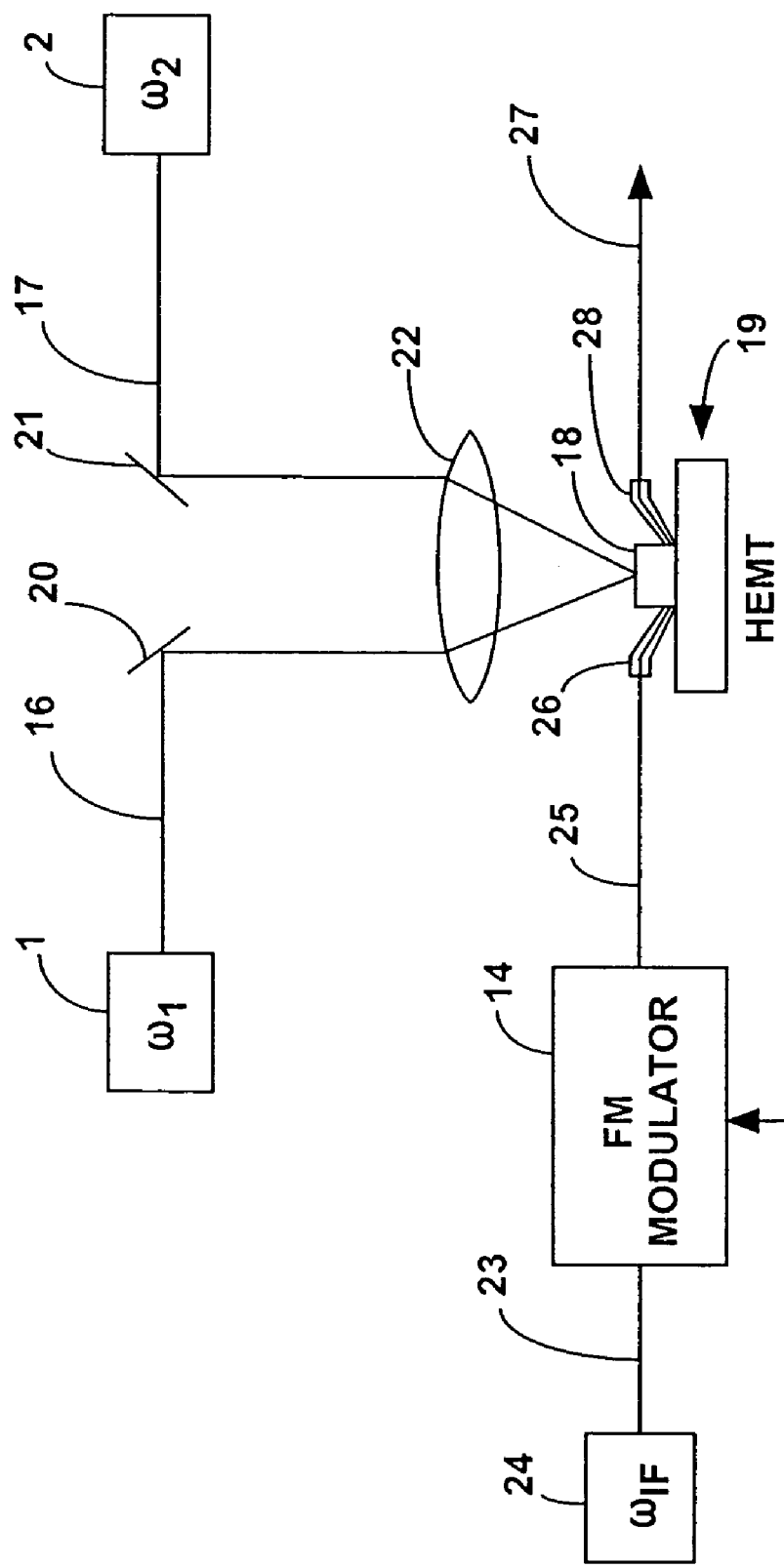
FIG. 7 shows a further embodiment of the system according to the present invention.

FIG. 7 shows an alternative embodiment, where the modulation can be also applied to the mixer itself, by combining the modulator 14 with the mixer through use of a three-terminal device, such as a high electron mobility pseudomorphic transistor (HEMT). A HEMT is described, for example, in M. E. Ali, K. S. Ramesh, H. R. Fetterman, M. Matloubian, and G. Boll, "Optical Mixing with Difference Frequencies to 552 GHz in Ultrafast High Electron Mobility Transistors" IEEE Photonics Technology Letters, Vol. 12, No. 7, July 2000, which is incorporated herein by reference.

The pair of unmodulated laser beams 16, 17 is incident upon the photoconductive region 18 of the HEMT 19, through mirrors 20, 21 and an objective lens 22 which focuses the incident beams 16, 17 on the photoconductive region 18. The FM modulator 14 has a modulation frequency $\Delta$ and receives an input signal 23 having a frequency $\omega_{IF}$ output from oscillator 24. The value of $f_{IF}$ is preferably in a range of 1 GHz to 100 GHz.

Figure 8:
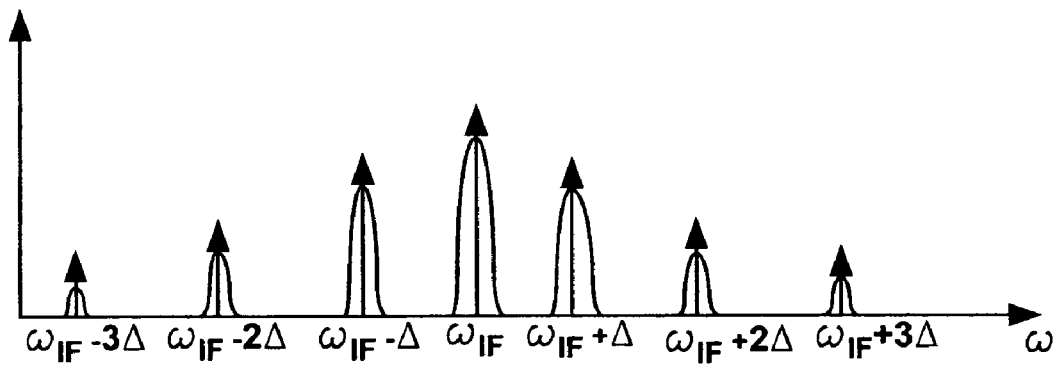
FIGS. 8 and 9 show frequency domain graphs relating to the system of FIG. 7.

FIG. 8 shows the frequency spectrum of the output signal 25 of the modulator 14. Turning to FIG. 7, the signal 25 is input to a second terminal 26 of the HEMT 19. The output 27 of the circuit of FIG. 7 is taken on the third terminal 28 of the HEMT 19. According to this embodiment, the HEMT transistor itself performs the function of the mixer.

Figure 9:
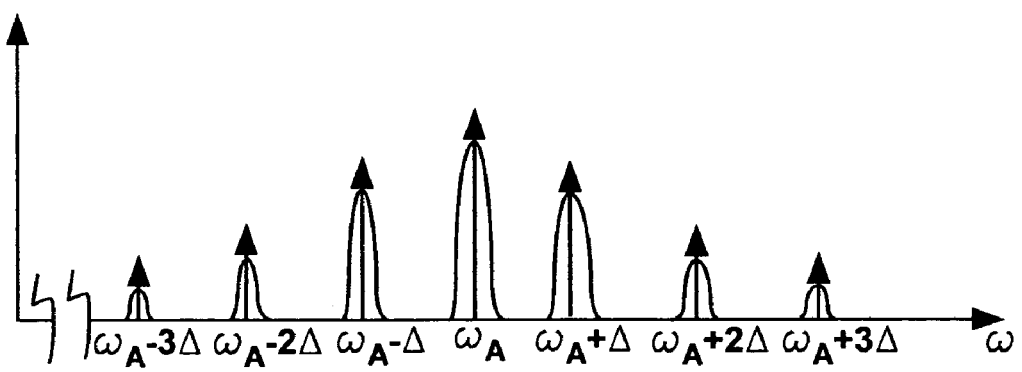

FIG. 9 shows the frequency spectrum of the output signal 27 of the circuit in FIG. 7, where $\omega_A=(\omega_1-\omega_2)-\omega_{IF}=\omega T-\omega_{IF}$. $\omega T$ is in the THz range, for example 100 THz. Usually, $\omega_{IF}$ is about 0.1% to 10% of $\omega_T$, and $\Delta$ is about 0.1% to 10% of $\omega_{IF}$.

Finally, also amplitude modulation formats (AM modulation spectroscopy) can be implemented using this invention. More specifically, the FM modulator is replaced by an amplitude modulator in all the embodiments. The various sidebands will still appear as before ($\delta\omega$, $\delta\omega\pm\Delta$, $\delta\omega\pm2\Delta$, $\delta\omega\pm3\Delta$, ... $\delta\omega\pm M\Delta$,) but with different phase relationship.

While several illustrative embodiments of the invention have been shown and described, numerous variations and alternative embodiments will occur to those skilled in the art. Such variations and alternative embodiments are contemplated, and can be made without departing from the scope of the invention as defined in the appended claims.

What is claimed is:

1. An apparatus comprising:
a first laser, emitting a first beam having a first frequency;
a second laser, emitting a second beam having a second frequency, the difference between the first frequency and the second frequency being in a Terahertz range;
a mixer, located downstream of the first laser and the second laser, the mixer producing a mixed signal adapted to be input to a sample whose spectral properties are to be detected, wherein the mixed signal has a frequency spectrum comprising a carrier component and at least two sideband components, the carrier component centered at a Terahertz frequency;
a modulator modulating at least one of the first and second beams; and
a detector to detect shift of one of said at least two sideband components relative to the carrier and to the other of said at least two sideband components.

2. The apparatus of claim 1, wherein the carrier component has a frequency displacement from the sideband components depending on the modulation of the at least one beam.

3. The apparatus of claim 1, wherein the modulator is combined with the mixer through use of a three-terminal device.

4. The apparatus of claim 3, wherein the three-terminal device is a high electron mobility pseudomorphic transistor.

5. The apparatus of claim 1, wherein the modulator is located upstream of the mixer.

6. The apparatus of claim 1, wherein the modulator performs frequency modulation of the at least one beam.

7. The apparatus of claim 1, wherein the modulator performs amplitude modulation of the at least one beam.

8. The apparatus of claim 1, wherein at least one of the first frequency, the second frequency and the modulator frequency is a tunable frequency.

9. An apparatus comprising:
a first laser, emitting a first beam having a first frequency;
a second laser, emitting a second beam having a second frequency, the difference between the first frequency and the second frequency being in a Terahertz range;
a frequency modulator, having a modulation frequency, for frequency modulating one of the first and second beams;
a mixer, having as an input the frequency modulated one beam and the other beam and outputting a mixed signal adapted to be input to a sample whose spectral properties are to be detected, wherein the mixed signal has a frequency spectrum comprising a carrier component and at least two sideband components, the carrier component centered at a Terahertz frequency; and a detector to detect shift of one of said at least two sideband components relative to the carrier and to the other of said at least two sideband components.

10. The apparatus of claim 9, wherein the mixed signal is tunable so that said one of said at least two sideband components is resonant with a spectral property to be detected.

11. The apparatus of claim 10, wherein the mixed signal is tunable by tuning the modulation frequency of the frequency modulator.

12. The apparatus of claim 10, wherein the mixed signal is tunable by tuning the difference between the first frequency and the second frequency.

13. The apparatus of claim 9, wherein the first laser and the second laser are narrowband lasers.

14. The apparatus of claim 9, wherein the first laser and the second laser have a frequency band in a range of about 1 KHz to about 10 MHz.

15. The apparatus of claim 9, wherein the first laser and the second laser are chosen from a group comprising laser diodes, fiber lasers, and diode-pumped solid state lasers.

16. An apparatus comprising:
a first laser, emitting a first beam having a first frequency;
a second laser, emitting a second frequency modulated beam having a carrier frequency and a modulation frequency, the difference between the first frequency and the carrier frequency being in a Terahertz range;
a mixer, having as an input the first beam and the second frequency modulated beam and outputting a mixed signal adapted to be input to a sample whose spectral properties are to be detected, wherein the mixed signal has a frequency spectrum comprising a carrier component and at least two sideband components, the carrier component centered at a Terahertz frequency; and
a detector to detect shift of one of said at least two sideband components relative to the carrier and to the other of said at least two sideband components.

17. The apparatus of claim 16, wherein the mixed signal is tunable so that said one of said at least two sideband components is resonant with a spectral property to be detected.

18. The apparatus of claim 17, wherein the mixed signal is tunable by tuning the modulation frequency.

19. The spectrometer of claim 17, wherein the mixed signal is tunable by tuning the difference between the first frequency and the second frequency.

20. An apparatus comprising:
a first laser, emitting a first beam having a first frequency;
a second laser, emitting a second beam having a second frequency, the difference between the first frequency and the second frequency being in a Terahertz range;
a modulator, for modulating in amplitude one of the first and second beams;
a mixer, having as an input the amplitude modulated one beam and the other beam and outputting a mixed signal adapted to be input to a sample whose spectral properties are to be detected, wherein the mixed signal has a frequency spectrum comprising a carrier component and at least two sideband components, the carrier component centered at a Terahertz frequency; and
a detector to detect shift of one of said at least two sideband components relative to the carrier and to the other of said at least two sideband components.

21. An apparatus comprising:
a first laser, emitting a first beam having a first frequency;
a second laser, emitting a second amplitude modulated beam having a carrier frequency, the difference between the first frequency and the carrier frequency being in a Terahertz domain;
a mixer, having as an input the first beam and the second amplitude modulated beam and outputting a mixed signal adapted to be input to a sample whose spectral properties are to be detected, wherein the mixed signal has a frequency spectrum comprising a carrier component and at least two sideband components, the carrier component centered at a Terahertz frequency; and
a detector to detect shift of one of said at least two sideband components relative to the carrier and to the other of said at least two sideband components.

22. An apparatus comprising:
a first laser, emitting a first beam having a first frequency;
a second laser, emitting a second beam having a second frequency, the difference between the first frequency and the second frequency being in a Terahertz range;
a high electron mobility transistor (HEMT) having a first terminal, a second terminal, and a photoconductive region on which the first beam and the second beam impinge;
a modulator having a modulation frequency, for modulating an intermediate signal having an intermediate frequency inferior to the first frequency and the second frequency to obtain a modulated signal, the modulated signal input to the first terminal of the HEMT,
wherein the second terminal of the HEMT outputs a mixed signal having a frequency spectrum depending on the first frequency, the second frequency, the intermediate frequency, and the modulation frequency, the mixed signal adapted to be input to a sample whose spectral properties are to be detected, wherein said frequency spectrum of the mixed signal comprises a carrier component and at least two sideband components, the carrier component centered at a Terahertz frequency; and
a detector to detect shift of one of said at least two sideband components relative to the carrier and to the other of said at least two sideband components.

23. The apparatus of claim 22, further comprising an oscillator emitting the intermediate signal at the intermediate frequency.

24. The apparatus of claim 22, further comprising an objective lens for focusing the first beam and the second beam on the photoconductive region of the HEMT.

25. A method comprising:
providing a first laser beam having a first frequency;
providing a second laser beam having a second frequency, the difference between the first frequency and the second frequency being a Terahertz frequency;
modulating at least one of the first and second beams; and
mixing the first beam and the second beam to generate a mixed signal, the mixed signal adapted to be input to a sample whose spectral properties are to be detected, the mixed signal having a frequency spectrum comprising a carrier and sidebands, wherein the spectral properties of the sample can be detected by detecting shift of at least one of said sidebands relative to the carrier and other sidebands.

26. The method of claim 25, wherein inputting the mixed signal to a sample comprises tuning the mixed signal to create resonance with the spectral properties of the sample.

* * * * *